(12) United States Patent
An et al.

(10) Patent No.: US 6,958,604 B2
(45) Date of Patent: Oct. 25, 2005

(54) APPARATUS AND METHODS FOR J-EDIT NUCLEAR MAGNETIC RESONANCE MEASUREMENT

(75) Inventors: Li An, Sugar Land, TX (US); Yi-Qiao Song, Ridgefield, CT (US); Krishnamurthy Ganesan, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 63 days.

(21) Appl. No.: 10/601,460

(22) Filed: Jun. 23, 2003

(65) Prior Publication Data

US 2004/0257075 A1 Dec. 23, 2004

(51) Int. Cl.⁷ .................................................. G01V 3/00
(52) U.S. Cl. .................................... 324/303; 324/300
(58) Field of Search ................................ 324/303, 300, 324/309, 307, 310; 436/173

(56) References Cited

U.S. PATENT DOCUMENTS

| | | | | |
|---|---|---|---|---|
| 5,043,664 A | * | 8/1991 | Kunz ........................ | 324/307 |
| 5,317,261 A | * | 5/1994 | Den Hollander et al. ... | 324/309 |
| 5,629,623 A | | 5/1997 | Sezginer et al. | |
| 5,914,598 A | | 6/1999 | Sezginer et al. | |
| 5,955,883 A | | 9/1999 | Hennig | |
| 6,104,191 A | * | 8/2000 | Hurd ........................ | 324/310 |
| 6,111,408 A | * | 8/2000 | Blades et al. ............... | 324/303 |
| 6,111,409 A | * | 8/2000 | Edwards et al. ........... | 324/303 |
| 6,140,812 A | | 10/2000 | Russell et al. | |
| 6,147,490 A | * | 11/2000 | Watanabe ................... | 324/307 |
| 6,232,778 B1 | | 5/2001 | Speier et al. | |
| 6,237,404 B1 | | 5/2001 | Crary et al. | |
| 6,246,236 B1 | | 6/2001 | Poitzsch et al. | |
| 6,255,817 B1 | | 7/2001 | Poitzsch et al. | |
| 6,291,995 B1 | | 9/2001 | Speier et al. | |

(Continued)

FOREIGN PATENT DOCUMENTS

| | | |
|---|---|---|
| EP | 0 514 978 A1 | 11/1992 |
| EP | 1 098 204 A1 | 5/2001 |
| GB | 2 396 016 A | 6/2004 |

OTHER PUBLICATIONS

EL Hahn & DE Maxwell, "Spin Echo Measurements of Nuclear Spin Coupling in Molecules," *Physical Rev.* 88, No. 5, pp. 1070–1084 (1952).

(Continued)

*Primary Examiner*—Brij B. Shrivastav
(74) *Attorney, Agent, or Firm*—Kevin P. McEnaney; Brigitte L. Echols; Victor H. Segura

(57) ABSTRACT

A method for obtaining nuclear magnetic resonance measurements includes inducing a static magnetic field in a formation fluid sample; applying an oscillating magnetic field to the fluid sample according to a preparation pulse sequence that comprises a J-edit pulse sequence for developing J modulation; and acquiring the nuclear magnetic resonance measurements using a detection sequence, wherein the detection sequence comprises at least one 180-degree pulse. The method may further include acquiring the nuclear magnetic resonance measurements a plurality of times each with a different value in a variable delay in the J-edit pulse sequence; and analyzing amplitudes of the plurality of nuclear magnetic resonance measurements as a function of the variable delay to provide J coupling information.

30 Claims, 9 Drawing Sheets

U.S. PATENT DOCUMENTS

| | | | |
|---|---|---|---|
| 6,297,632 B1 | 10/2001 | Speier | |
| 6,326,784 B1 | 12/2001 | Ganesan | |
| 6,346,813 B1 | 2/2002 | Kleinberg | |
| 6,366,089 B1 | 4/2002 | Poitzsch et al. | |
| 6,373,248 B1 | 4/2002 | Poitzsch et al. | |
| 6,392,410 B2 | 5/2002 | Luong et al. | |
| 6,400,149 B1 | 6/2002 | Luong et al. | |
| 6,472,870 B1 * | 10/2002 | Bendall et al. | 324/307 |
| 6,492,809 B1 | 12/2002 | Speier et al. | |
| 6,518,757 B1 | 2/2003 | Speier | |
| 6,518,758 B1 | 2/2003 | Speier et al. | |
| 6,528,995 B1 | 3/2003 | Speier et al. | |
| 6,531,869 B1 | 3/2003 | Speier et al. | |
| 6,538,438 B1 | 3/2003 | Speier et al. | |
| 6,566,874 B1 | 5/2003 | Speier et al. | |
| 6,570,381 B1 | 5/2003 | Speier et al. | |
| 6,617,169 B2 * | 9/2003 | Ke et al. | 436/173 |
| 2002/0075000 A1 | 6/2002 | Prammer et al. | |

OTHER PUBLICATIONS

L Muller, A Kumar & RR Ernst, "Two-dimensional Carbon-13 NMR Spectroscopy," *J. Phys. Chem. 63*, pp. 5490–5491 (1975).

FD Doty, RR Inners & PD Ellis, "A Multinuclear Double-Tuned Probe for Applications with Solids or Liquids utilizing Lumped Tuning Elements," *J. Magnetic Res. 43*, pp. 399–416 (1981).

MH Levitt, "Symmetrical Composite Pulse Sequences for NMR Population Inversion," *J. Magnetic Res. 48*, pp. 234–264 (1982).

MH Leavitt & R Freeman, "NMR Population Inversion using a Composite Pulse," *J. Magnetic Res. 33*, pp. 473–476 (1979).

SR Hartmann & EL Hahn, "Nuclear Double Resonance in the Rotating Frame," *Phys. Rev. 128*, No. 5, pp. 2042–2053 (1962).

GA Morris & R Freeman, "Enhancement of Nuclear Magnetic Resonance Signals by Polarization Transfer," *J. Am. Chem. Soc. 101*, No. 3, pp. 760–762 (1970).

LA Davis et al., "The Modulation of Coupled Relaxation in Porous Media," *Magnetic Resonance Imaging 19* (pp. 369–373 (2001).

TJ Norwood et al., "Measurement of the Scalar Coupling and Transverse Relaxation Times of Doublets," *Journal of Magnetic Resonance Series A 101*, pp. 109–112 (1993).

* cited by examiner

APPARATUS AND METHODS FOR J-EDIT NUCLEAR MAGNETIC RESONANCE MEASUREMENT

CROSS-REFERENCE TO RELATED APPLICATIONS

Not Applicable.

BACKGROUND OF INVENTION

1. Field of the Invention

The invention relates generally to well logging using nuclear magnetic resonance (NMR) instruments. More specifically, the present invention relates to methods and apparatus for NMR well logging based on carbon-proton J-coupling.

2. Background Art

Oil and gas exploration and production are very expensive operations. Any knowledge about the formations that can help reduce the unnecessary waste of resources in well drilling will be invaluable. Therefore, the oil and gas industry have developed various tools capable of determining and predicting earth formation properties. Among different types of tools, nuclear magnetic resonance (NMR) instruments have proven to be invaluable. NMR instruments can be used to determine formation properties, such as the fractional volume of pore space and the fractional volume of mobile fluid filling the pore space. General background of NMR well logging is described in U.S. Pat. No. 6,140,817.

Nuclear magnetic resonance is a phenomenon occurring in a selected group of nuclei having magnetic nuclear moments, i.e., non-zero spin quantum numbers. When these nuclei are placed in a magnetic field ($B_o$, "Zeeman field"), they each precess around the axis of the $B_o$ field with a specific frequency, the Larmor frequency ($\omega_o$), which is a characteristic property of each nuclear species (gyromagnetic ratio, $\gamma$) and depends on the magnetic field strength ($B_o$) effective at the location of the nucleus, i.e., $\omega_o = \gamma B_o$.

Proton is the major nucleus of investigation in well logging NMR applications because of its good NMR sensitivity and its high abundance in water and hydrocarbons. Furthermore, due to downhole limitations, the current well logging tools only measure $T_1$, $T_2$ relaxation times and diffusion effects.

In other fields of NMR applications such as chemistry, biology, and petroleum fluid analysis, proton and carbon chemical shift and J-coupling spectroscopic techniques are routinely used to determine molecular structures. Chemical shift is the term given to describe the screening effect of the electrons to the magnetic field that a nucleus experiences. Different chemical groups, such as $CH_2$ and $CH_3$, have different magnitude of screening effects, and, therefore, they appear as separate peaks in the proton chemical shift spectrum. The separation in frequency of different peaks is proportional to the static magnetic field strength, i.e., magnetic, field dependent. J-coupling, also known as spin-spin or scalar coupling, originates from spin interaction between nuclei through bonding electrons. See, E. L. Hahn, and D. E. Maxwell, *Spin echo measurements of nuclear spin coupling in molecules*, Physical Review 88, 1070–1084 (1952). J-coupling experiment is seldom performed by itself. Instead, J couplings are always measured together with chemical shifts through one-dimensional or multi-dimensional spectroscopic techniques.

As noted above, chemical shift is magnetic field dependent. The homogeneity of a static magnetic field has to be within a few parts per million (ppm) to perform chemical shift spectroscopy. This level of homogeneity is hard to realize in the wellbore using existing technologies. In contrast, J-coupling constants are independent of static magnetic field strengths and temperatures. This makes it possible to perform J-coupling experiment without chemical shift spectroscopy in inhomogeneous static and radio-frequency (RF) magnetic fields.

U.S. Pat. No. 6,111,409 issued to Edwards discloses methods for performing chemical shift spectroscopy in the wellbore. Because the static magnetic field homogeneity is difficult to achieve in the formation, the methods of Edwards involve withdrawing fluids into a formation tester before NMR measurements. Even in the formation tester, the stringent homogeneity required for conventional chemical shift measurements is not an easy task. A permanent magnet and shim coils will be used to generate the static magnetic field. First of all, the space in the tool that can accommodate the magnet and shim coils is very limited in shape and size. To achieve a 1 ppm homogeneity over a reasonable volume is a daunting task for magnet design and manufacturing. If the homogeneous volume is too small, the small sample may not be a good representation of the fluid being investigated. Secondly, temperature change can affect the strength and homogeneity of the magnetic field.

U.S. Pat. No. 6,346,813 issued to Kleinberg discloses a variety of NMR measurements for characterizing fluid samples withdrawn from subsurface formations. This patent is assigned to the assignee of the present invention and is hereby incorporated by reference. Proton and carbon. NMR measurements are among the proposed techniques.

U.S. patent application Ser. No. 10/064,529 filed by Speier on Jul. 24, 2002, discloses methods for J-spectroscopy experiments using spin-echo difference techniques. This application is assigned to the assignee of the present invention and is hereby incorporated by reference. This approach provides convenient methods to obtain J couplings in the wellbore. Although this approach is less sensitive to magnetic field inhomogeneity, it still suffers from field inhomogeneity to some extent. The inhomogeneous, $B_0$ (static) field makes the effective $B_1$ (radio-frequency) field inhomogeneous. As a result, the $\pi$ pulses may not be accurate throughout the region of investigation. Inaccurate $\pi$ pulses may diminish the J-modulation signals.

Therefore, it is desirable to have NMR methods and apparatus for determining J coupling that are less affected by magnetic field inhomogeneity.

SUMMARY OF INVENTION

In one aspect, embodiments of the invention relate to methods for performing nuclear magnetic resonance measurements having J modulation information. A method for obtaining nuclear magnetic resonance measurements in accordance with one embodiment of the invention includes inducing a static magnetic field in a formation fluid sample; applying an oscillating magnetic field to the fluid sample according to a preparation pulse sequence that comprises a J-edit pulse sequence for developing J modulation; and acquiring the nuclear magnetic resonance measurements using a detection sequence, wherein the detection sequence comprises at least one 180-degree pulse. The method may further include acquiring the nuclear magnetic resonance measurements a plurality of times each with a different value in a variable delay in the J-edit pulse sequence; and analyzing amplitudes of the plurality of nuclear magnetic resonance measurements as a function of the variable delay to provide J coupling information.

Another aspect of the invention relates to methods for characterizing formation fluids. A method for characterizing formation fluids in accordance with one embodiment of the invention includes providing a nuclear magnetic resonance instrument in a borehole; inducing a static magnetic field in a region of interest; applying an oscillating magnetic field to the region of interest according to a preparation pulse sequence that comprises a J-edit pulse sequence for developing J modulation; and acquiring nuclear magnetic resonance measurements using a detection sequence, wherein the detection sequence comprises at least one 180-degree pulse.

Another aspect of the invention relates to nuclear magnetic resonance instruments for well logging. A nuclear magnetic resonance instrument in accordance with one embodiment of the invention includes a housing adapted to move in a wellbore; a magnet disposed in the housing adapted to induce a static magnetic field in a zone of interest; an antenna assembly disposed in the housing, the antenna assembly adapted to induce an oscillating magnetic field in the zone of interest and to receive nuclear magnetic resonance signals; and an electronic module including a memory to store instructions for performing a J-edit pulse sequence Other aspects of the invention will become apparent from the following description, the drawings, and the claims.

DETAILED DESCRIPTION

Embodiments of the invention relate to apparatus and methods for NMR well logging based on J-couplings (e.g., $^1H$—$^{13}C$). Embodiments of the invention are based on measuring the effects of J-coupling (e.g., $^1H$—$^{13}C$) on spin echo amplitudes. Methods in accordance with the invention are less sensitive to magnetic field inhomogeneity. Modulation of spin echo amplitudes by the J-coupling effects is referred to as "J-editing" in this description. J-editing can be used to determine detailed compositions of an oil sample, for example, the abundances of various carbon groups. These carbon groups may include quaternary C, aromatic CH, aliphatic CH, $CH_2$, $CH_3$, and $CH_4$.

Methods of the invention may be practiced with an NMR instrument similar to those known in the art. The NMR instrument may be in the laboratory or be part of a wireline logging tool, a measurement-while-drilling (MWD) tool, or a logging-while-drilling (LWD) tool. In addition, the NMR instrument may be part of a formation tester (fluid sampling tool) used to analyze the fluids withdrawn from the formations.

Figure 1:
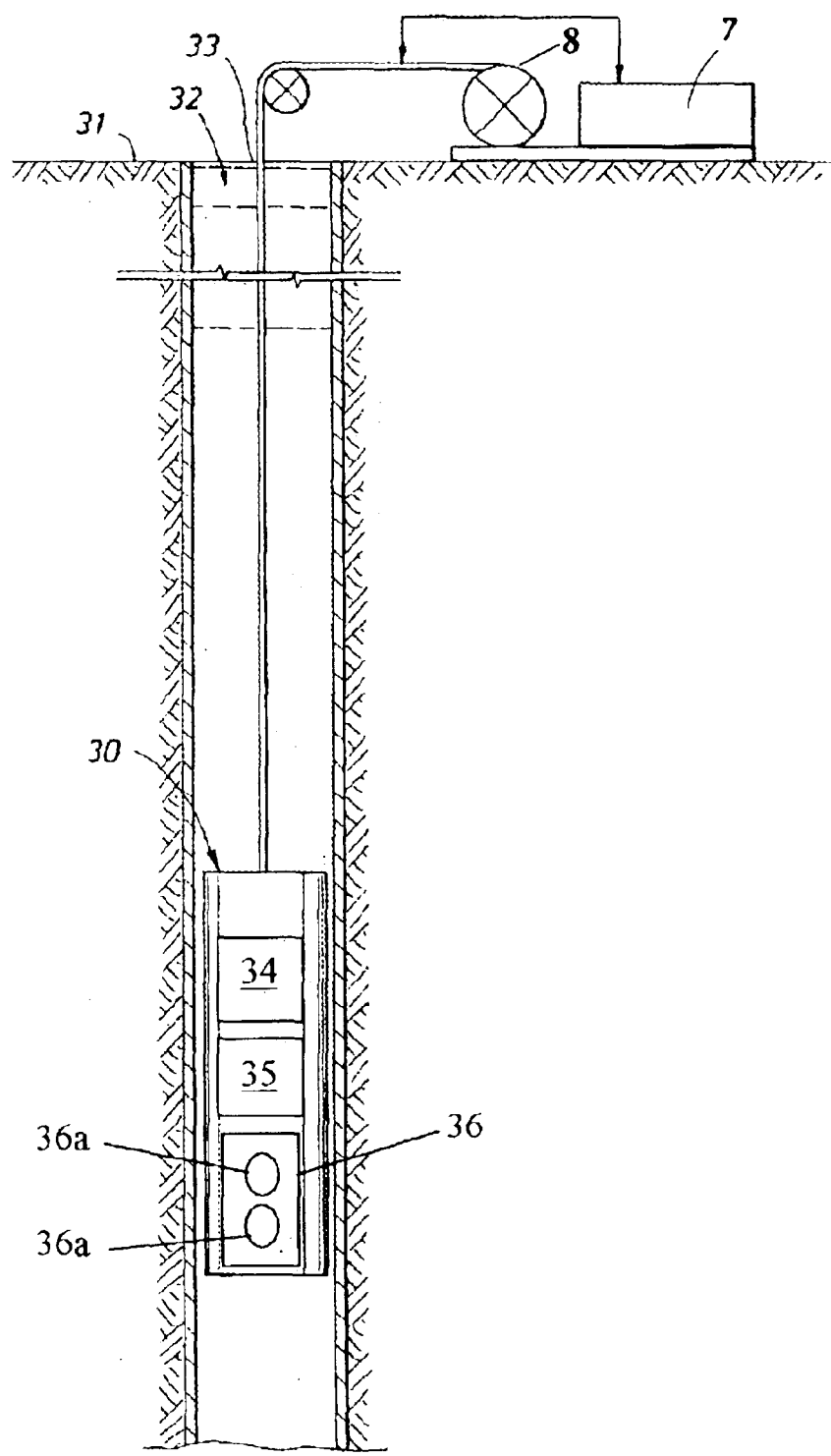
FIG. 1 shows a schematic diagram of an NMR logging tool in a well bore suitable for practicing methods of the invention.

FIG. 1 illustrates a schematic of an NMR well logging tool 30 placed in a wellbore 32 that penetrates a formation 31. The NMR logging tool 30 is suspended in well bore 32 on an armored cable 33, the length of which substantially determines the relative depth of the tool 30. The cable length is controlled by suitable means at the surface such as a drum and winch 8. Surface equipment 7 may comprise a processor which communicates with the downhole equipment. Although a wireline tool is shown in FIG. 1, variations of NMR logging tools may include MWD or LWD tools. The tool 30 may include one or more permanent magnets, represented as block 34, and one or more antennae (e.g., an antenna assembly), represented as block 35, that can induce RF (or oscillating) magnetic field and function as receivers. In addition, the tool 30 may include an electronic module 36, which may include a central processor 36a, a memory 36b, and other components (not shown) for controlling the pulse sequences and the acquisition. The memory 36b may store instructions for performing the J-edit pulse sequence in accordance with embodiments of the invention.

J-editing is based on the presence of J couplings between different nuclei, such as between different protons (homonuclear coupling) and between carbons and protons (heteronuclear coupling). See e.g., L. Muller, A. Kumar, and R. R. Ernst, *Two-dimensional carbon-13 NMR spectroscopy*, J. Chem. Phys. 63, 5490–5491 (1975). While methods of the invention may be applied to both homo- and hetero-nuclear couplings, for clarity, the following description uses only hetero-nuclear coupling experiments as illustrations. In addition, the following description uses carbon-proton coupling as an example. However, one of ordinary skill in the art would appreciate that methods of the invention may also be applied to other homonuclear or heteronuclear couplings.

A method in accordance with the invention generally comprises two parts. In the first part, the precession of observed spins (e.g., carbon) due to J-coupling to coupled spins (e.g., proton) is produced, resulting in an NMR signal of observed spins (e.g., carbon) that is a function of the J-coupling and some parameters of the pulse sequence. The pulse sequences used in the first part for developing J coupling effects are referred to as "J-edit pulse sequences" in this description. In the second part, the J-modulated observed spin (e.g., carbon) signal is detected, preferably using a pulse sequence (e.g., a $\pi$ pulse train as in a Carr-Purcell-Meiboom-Gill, CPMG, sequence) that maximizes signal-to-noise ratios (SNR). The pulse sequences used in the second part are referred to as "detection sequences." One of ordinary skill in the art would appreciate that various detection sequences, including CPMG-like sequences, may be used without departing from the scope of the invention. Thus, a complete pulse sequence in accordance with some embodiments of the invention comprises a J-edit pulse sequence followed by a detection sequence. In some embodiments of the invention to be described later, a complete pulse sequence may further include a signal enhancement pulse sequence (e.g., nuclear Overhauser effect (NOE) or magnetization transfer pulse sequences) before or after the J-edit pulse sequence. The pulse sequences before the detection pulse sequence is generally referred to as a "preparation pulse sequence." Thus, a preparation pulse sequence may include only a J-edit pulse sequence or additionally include a signal enhancement pulse sequence.

In J-editing experiments, radio frequency (RF) pulses at both carbon and proton resonance frequencies are generated and transmitted to the probe. The probe can use either one or two RF coils to induce and detect proton and carbon NMR signals. If two coils are used, one coil is tuned to the proton resonance frequency and the other to the carbon frequency. If one coil is used, the coil is double-tuned to both proton and carbon resonance frequencies. For one example, see F. D. Doty, R. R. Inners, and P. D. Ellis, *A multinuclear double-tuned probe for applications with solids or liquids utilizing lumped tuning elements*, J. Magn. Reson. 43, 399–416 (1981). Those of ordinary skill in the art would appreciate that other techniques may be used to induce and detect signals. An antenna assembly is used to refer to such coils, whether a single coil or two coils.

J-editing methods in accordance with the invention may be categorized into two basic groups—carbon detection methods and proton detection methods. In carbon detection methods, $^{13}C$ spins are the source of magnetization and the subject of detection (i.e., the observed spins), and the proton spins (i.e., the coupled spins) are flipped or decoupled to impose a J-modulation on the $^{13}C$ spin echo amplitude. This is conventionally denoted as $^{13}C\{^1H\}$, in which the nucleus before the bracket is the observed nucleus and the nucleus in the bracket is the coupled/decoupled nucleus. In proton detection methods, proton spins are the source of magnetization and the subject of detection (i.e., the observed spins), and the $^{13}C$ spins (i.e., the coupled spins) are flipped or decoupled to modulate the proton spin echo amplitude through J-coupling. This is conventionally denoted as, $^1H\{^{13}C\}$. The signal contribution from protons attached to $^{12}C$ is not modulated by the J-coupling and, therefore, may be removed by subtracting the signals of two scans, one with J-modulation and the other without.

The NMR sensitivity of $^{13}C$ detection is low compared to that of proton detection because of the low gyromagnetic ratio ($\gamma$) and the low natural abundance (about 1.1%) of the $^{13}C$ species. This makes it desirable to enhance the sensitivity of the carbon detection J-editing experiments. A variety of signal enhancement techniques may be used for this purpose. The signal enhancement techniques that may be used with embodiments of the invention, for example, may include nuclear Overhauser enhancement (NOE) techniques and magnetization transfer techniques. See G. A. Morris, and R. Freeman, *Enhancement of nuclear magnetic resonance signals by polarization transfer*, J. Am. Chem. Soc. 101:3, 760–762 (1979); S. L. Hartmann and E. L. Hahn, *Nuclear double resonance in the rotating frame*, Phys. Rev. 128, 2042–2053 (1962).

J-editing with Carbon Detection

Carbon detection J-editing methods have two subgroups: proton flip methods and gated decoupling methods. These methods will be described in more detail in the following sections.

Figure 2:
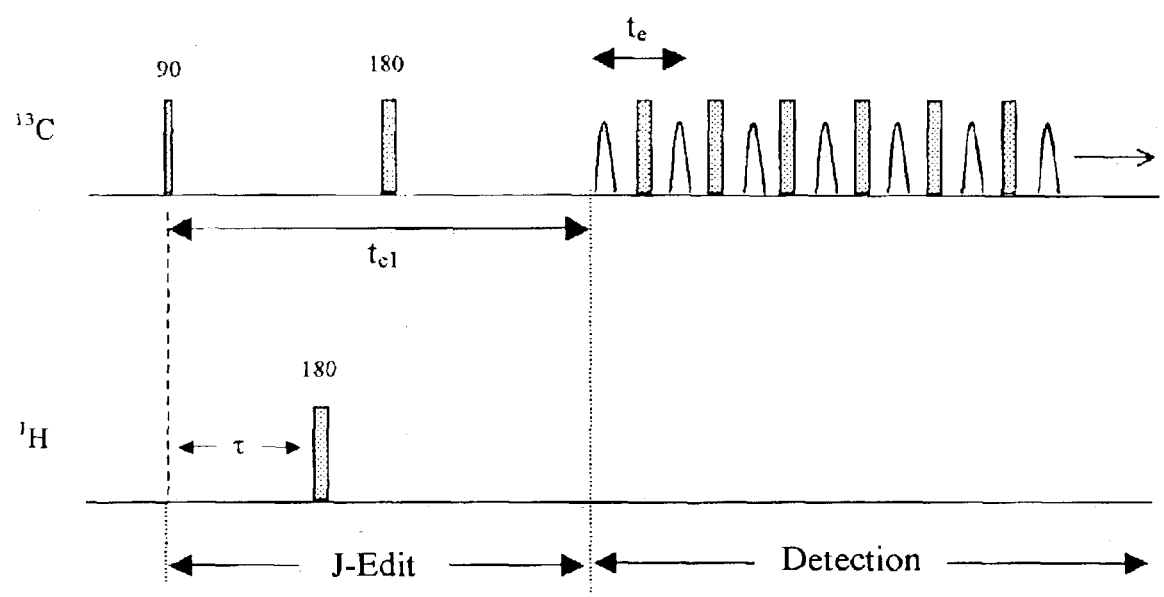
FIG. 2 shows a schematic diagram showing a pulse sequence for J editing according to one embodiment of the invention.

FIG. 2 shows a method according to one embodiment of the invention. This method uses a proton flip pulse in the decoupler channel to develop J modulation in the observation (e.g., $^{13}C$) channel. The pulse sequence as shown in FIG. 2 may be separated into two parts. The first part comprises a preparation pulse sequence that includes only a J-edit pulse sequence during the J-modulation period. The J-edit pulse sequence includes a typical spin-echo (($\pi/2$)-delay-($\pi$)-delay) pulse sequence in the $^{13}C$ channel and a $\pi$ pulse in the $^1H$ channel. The second part comprises a detection sequence that includes a train of $\pi$ pulses, as in a typical Carr-Purcell-Meiboom-Gill (CPMG) pulse, for the measurement of the spin echoes. Such a $\pi$ pulse train in the detection sequence is generally referred to as a CPMG-like sequence in this description.

As shown in FIG. 2, the first echo spacing for carbon ($t_{e1}$) is usually large, e.g., on the order of $1/J \approx 5$–$8$ ms, such that the J modulation would have sufficient time to develop. The later echoes ($t_e$) in the CPMG-like sequence preferably have short echo spacing (e.g. 200 $\mu s$) so that a large number of echoes may be acquired to improve SNR before diffusion and $T_2$ decays reduce signal amplitudes.

As shown in FIG. 2, a single $\pi$ pulse is applied in the proton channel at time $\tau$ after the first $\pi/2$ carbon pulse. Because of the C—H J coupling, after the initial $\pi/2$ carbon pulse, the carbon magnetization splits into two vectors precessing around the static magnetic field $B_0$ at two different angular frequencies. The changing phase angle (separation) between the two vectors causes the total magnetization amplitude to change as a cosine function of the phase angle. In other words, the amplitude of the carbon magnetization is J-modulated. During the $\tau$ period, the phase angle (separation) between the two vectors gradually increases, until the proton $\pi$ pulse exchanges the angular frequencies of the two vectors. As a result of the proton $\pi$ pulse, which exchanges the spin states of the proton spins, the phase angle between the two vectors decreases until the carbon $\pi$ pulse is applied. The carbon $\pi$ pulse exchanges the spin states of the carbon spins, and hence the angular frequencies of the two vectors are exchanged again. Thus, the phase angle (i.e., phase separation between the two vectors) increases again. From this description, it is clear that J modulation only occurs during a period corresponding to $2\tau$ within the first echo spacing. In other words, the extent of J modulation depends on the delay time $\tau$. This J modulation manifests itself as a J-modulation factor that modulates the first echo amplitude.

After the first echo, only carbon $\pi$ pulses are applied to the carbon channel to generate an echo train, but no proton pulses are applied to the proton channel. As a result, the carbon $\pi$ pulses, which are applied in the middle of the echo spacings, suppress further J modulation. As a result, J modulation occurs only during the first echo spacing, i.e., the J-modulation factor is frozen after the first echo and all subsequent echoes have the same J modulation as the first echo. Because all echoes have the same J-modulation factor, it is possible to sum up all echoes to improve the signal-to-noise ratio (SNR) without losing J-modulation information. When all echoes are summed up, the $T_2$ and diffusion decay effects in the second and subsequent echoes are ignored. This has little effect on the derivation of the J-modulation factor. Alternatively, the J-modulation factor may be found by a fitting procedure where $T_2$ and diffusion decay effects in the second and subsequent echoes are taken into account.

As noted above, J modulation is frozen after the first echo. Therefore, the J-modulation factor may be derived from the first echo amplitude $S(\tau)$. Without considering the effects of static and RF field inhomogeneities, $S(\tau)$ is given by $$S(\tau) = S_0^c \sum_i A_i (\cos 2\pi J_i \tau)^{n_i} \quad \text{Eq. (1)}$$

where $S_0^c$ is the carbon spin echo amplitude without the J modulation, $A_i$ is the relative abundance of the $i^{th}$ carbon group, $J_i$ the proton-carbon J-coupling constant for the $i^{th}$ carbon group, and $n_i$ is the number of protons in the $i^{th}$ carbon group.

Eq. (1) shows that with a fixed $\tau$, the amplitude of the first echo (or the sum of all echoes) is related to cosine functions of the coupling constant ($J_i$) to the $n_i$-th power, where $n_i$ is the number of protons attached to the carbon. The number of protons ($n_i$) attached to a carbon may have five different values: 0 for C (quaternary carbon), 1 for CH, 2 for $CH_2$, 3 for $CH_3$, and 4 for $CH_4$. The number of protons ($n_i$=1–4) attached to a carbon has little effect on the C—H J-coupling constants. For example, C—H coupling constants for all aliphatic carbons (CH, $CH_2$, $CH_3$, and $CH_4$) are around 125 Hz.

In Eq. (1), carbon groups are defined in such a way that different carbon groups either have different J-coupling constants ($J_i$) or different number of protons ($n_i$) Because J-coupling constants do not vary much, it is convenient to group the J-coupling constants into a few values. For example, all the J-coupling constants in an oil sample may be approximately grouped into two values: 160 Hz for aromatic carbon groups and 125 Hz for aliphatic carbon groups. By doing so, the oil sample may have six different carbon groups, which are listed in table 1. For typical oil samples, there is little aliphatic CH and most of the CH is in aromatics. Thus, the aliphatic CH group may be ignored to simplify the model, if desired.

TABLE 1

An example of carbon group modeling

| Carbon group index i | Name | C—H coupling constant $J_i$ | Number of protons $n_i$ |
|---|---|---|---|
| 1 | Quaternary C | None | 0 |
| 2 | Aromatic CH | 160 Hz | 1 |
| 3 | Aliphatic CH | 125 Hz | 1 |
| 4 | $CH_2$ | 125 Hz | 2 |
| 5 | $CH_3$ | 125 Hz | 3 |
| 6 | $CH_4$ | 125 Hz | 4 |

With a particular sample, the distributions of $J_i$ and $n_i$ do not change, if a series of measurements are acquired with different delay times, the amplitudes of the first echoes in these measurements would depend on cosine functions of the delay time $\tau$. According to a preferred embodiment of the invention, multiple scans with different $\tau$ values may be acquired with a fixed first echo spacing such that the $T_2$ and diffusion effects are the same for all measurements. When these measurements are acquired with different delay times $\tau$, the amplitudes of these measurements would depend on the delay times $\tau$. The signal amplitudes as a function of $\tau$ would form a set of linear equations, from which $A_i$, the abundances of different carbon groups, may be computed.

In solving these linear equations, the J-coupling constants may be obtained from the published values in the literature or from lab NMR spectroscopic experiments on oil samples. As noted above, the J coupling constants do not vary significantly among all aliphatic carbon groups and these coupling constants can be approximated with a few values that depend on the hybridization of the carbon (e.g., the values shown in Table 1).

In the above described approach, a set of linear equations may be obtained with a plurality of different $\tau$ values, which need not have any particular relationship to each other. In an alternative approach, a plurality of measurements may be acquired with uniformly incremented $\tau$ values. With such a data set, Fourier transform may be used to produce a J spectrum, from which $J_i$ and $A_i$ may be derived.

Figure 3:
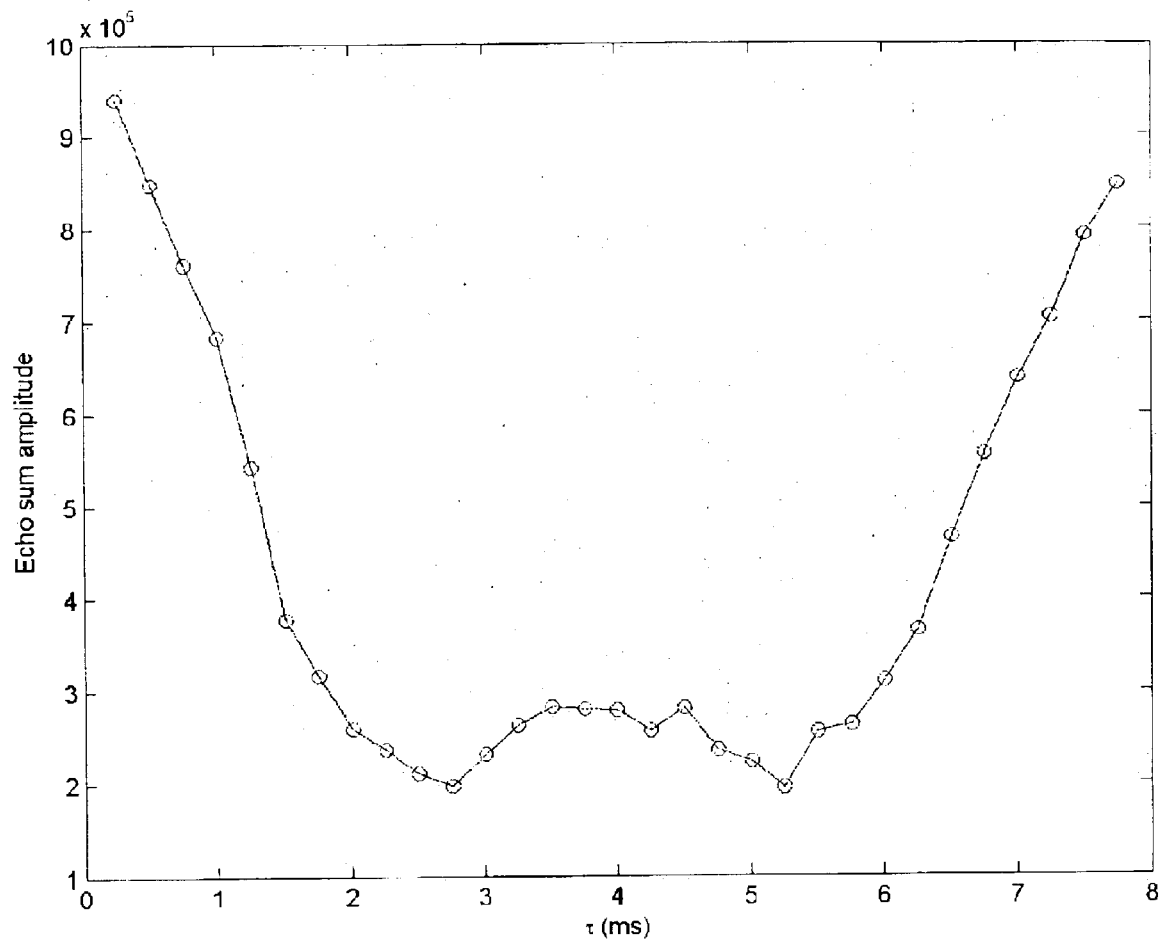
FIG. 3 shows a graph of signal amplitudes as a function of the delay time for J modulation according to one embodiment of the invention.

FIG. 3 shows an example graph of echo amplitudes as a function of $\tau$ delays using a light oil sample. This example includes 31 $\tau$ values from 0–8 ms. The modulation of the echo amplitudes by the $\tau$ delays is apparent from this graph. It is clear from this graph that a majority of the echo amplitudes is modulated by a J coupling that manifests itself as a periodicity of about 8 ms in this graph. This periodicity corresponds to a J coupling constant of about 125 Hz, indicating that the majority of signals are from aliphatic carbon groups. This is consistent with the composition of the sample.

FIG. 2 illustrates only a basic scheme for a method in accordance with the present invention. One of ordinary skill in the art would appreciate that other techniques known in the art may be included to improve the measurements. For example, phase cycling may be included to reduce or suppress constant noises (e.g., DC offset of the instrument) or signal degradation due to imperfect pulse lengths (i.e., the $\pi/2$ or $\pi$ pulse). Thus, the use of phase cycling is expressly within the scope of the present invention. Examples of the phase cycling schemes include CYCLOPS, which can be used to remove DC offset and unbalanced gains in quadrature detection. In addition, cycling of the first $\pi/2$ pulse can remove the extra carbon magnetization recovered due to $T_1$ relaxation during the long train of CPMG-like $\pi$ pulses.

Furthermore, one of ordinary skill in the art would appreciate that the $\pi/2$ and $\pi$ pulses depicted in FIG. 2 may be substituted with composite pulses. Various composite $\pi/2$ and $\pi$ pulses are known in the art. See M. H. Levitt and R. Freeman, *J. Mag. Reson.* (33), 473 (1979). For example, a composite four-pulse sequence, $P=(\pi/4)_{-y}(\pi/4)_x(\pi/4)_y(\pi/4)_x$, is commonly used as a substitute for a $\pi/2$ pulse in the X-axis direction, $(\pi/2)_x$. See M. H. Levitt, *J Mag. Reson.* (48), 234 (1982). Similarly, a $\pi$ pulse, may be substituted by, for example, the following composite pulse: $P=(\pi/2)_x(\pi)_y(\pi/2)_x$. These composite $\pi/2$ or $\pi$ pulses typically produce better results because they are less prone to signal degradation due to imperfect pulse lengths for the $\pi/2$ or $\pi$ pulses. The pulse length imperfection is expected to be more severe in the downhole environment, where the temperature is expected to have a significant impact on the characteristics of the intricate circuitry in the pulse programmer and transmitter.

Note that the use of composite pulses is expressly within the scope of the present invention.

As shown in FIG. 2, the proton π pulse is applied after a delay time τ. This proton π pulse does not need to go past the first carbon π pulse (i.e., $\tau \leq t_{e1}/2$). However, embodiments of the invention are not so limited. In some embodiments, the proton π pulse may coincide with the first carbon π pulse (see FIG. 4). In other embodiments, the proton π pulse may go past the first carbon π pulse. In this case, τ is defined as the time delay between the proton π pulse and the first echo such that Eq. (1) still holds.

Figure 4:
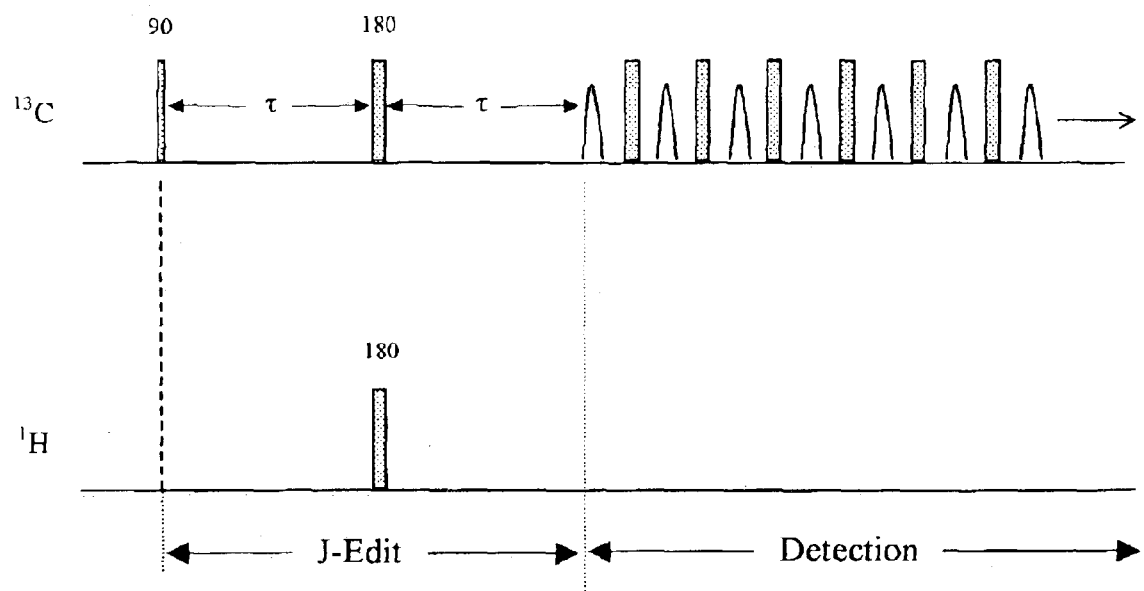
FIG. 4 shows a schematic diagram showing a pulse sequence for J editing according to one embodiment of the invention.

FIG. 4 shows a pulse sequence for another proton flip method in accordance with embodiments of the invention. In this pulse sequence, the proton π pulse and the carbon π pulse are applied simultaneously or with a fixed time shift. The first echo spacing and τ are varied to produce different J modulations. In this case, the first echo spacing is defined as 2τ and Eq. (1) still holds. With this pulse sequence, the $T_2$ and diffusion effects will be different when τ (hence the first spacing) is varied. Therefore, if a series of measurements are acquired with a plurality of τ values, correction may need to be applied to remove/correct the $T_2$ and diffusion effects in these measurements before these data are analyzed according to methods described above (e.g., solving a set of linear equations or performing a Fourier transformation).

As shown in FIG. 2 and FIG. 4, a pair of carbon/proton π pulses are applied during the first echo spacing, but only carbon π pulses are applied during the subsequent echo spacings in the CPMG-like pulse train. With this pulse sequence, J modulation builds up during the first echo spacing only. One of ordinary skill in the art would appreciate that other modifications to these pulse sequences are possible without departing from the scope of this invention. For example, it is also possible to build up the J-modulation during the first few echo spacings. During each of these early echo spacings, which should be relatively long (e.g., 8 ms) for J modulation to develop, a pair of carbon and proton π pulses are applied, as shown for the first echo spacing in FIG. 2 and FIG. 4. One of ordinary skill in the art would also appreciate that this technique of using multiple pairs of carbon/proton π pulses to build up J-modulation in the first few echo spacings may be applied to all proton-flip carbon-detection methods and carbon-flip proton-detection methods which will be described later.

Figure 5:
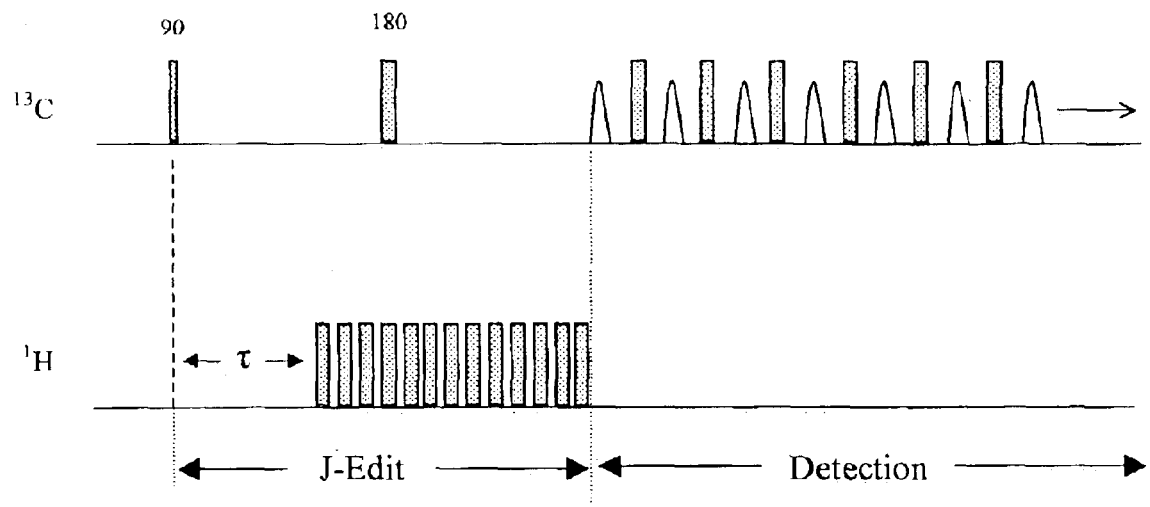
FIG. 5 shows a schematic diagram showing a pulse sequence for J editing including gated decoupling according to one embodiment of the invention.

J modulation may be created with π pulses (flip pulses) or with gated decoupling in the coupled nuclei channel. Some embodiments of the invention use gated decoupling, instead of flip pulses. FIG. 5 shows one such pulse sequence, in which a proton decoupling replaces the proton π pulse in FIG. 2. The proton decoupling stops J-modulation buildup from time τ to the first echo. Thus, J modulation develops only during τ period using the pulse sequence of FIG. 5 as opposed to 2τ period using the pulse sequence of FIG. 2. As a result, the first echo amplitude S(τ) from the experiment shown in FIG. 5 is given by:

$$S(\tau) = S_0^c \sum_i A_i (\cos \pi J_i \tau)^{n_i} \qquad \text{Eq. (2)}$$

In a related pulse sequence, the proton decoupling may be applied right after the carbon π/2 pulse and be removed at some point before the first echo. In this case, τ is defined as the time delay between the end of the decoupling pulse and the first echo and Eq. (2) still holds. One of ordinary skill in the art would appreciate that proton decoupling as depicted in FIG. 5 may be accomplished by any composite pulses known in the art for decoupling or with a broad-band (e.g., noise modulation) decoupling pulse. In addition, while FIG. 5 shows that $^{13}$C is the observed spin and $^1$H is the coupled spin (i.e., $^{13}$C{$^1$H}) for clarity of illustration, these pulse sequences may also be applied to other hetero nuclear combinations.

Figure 6:
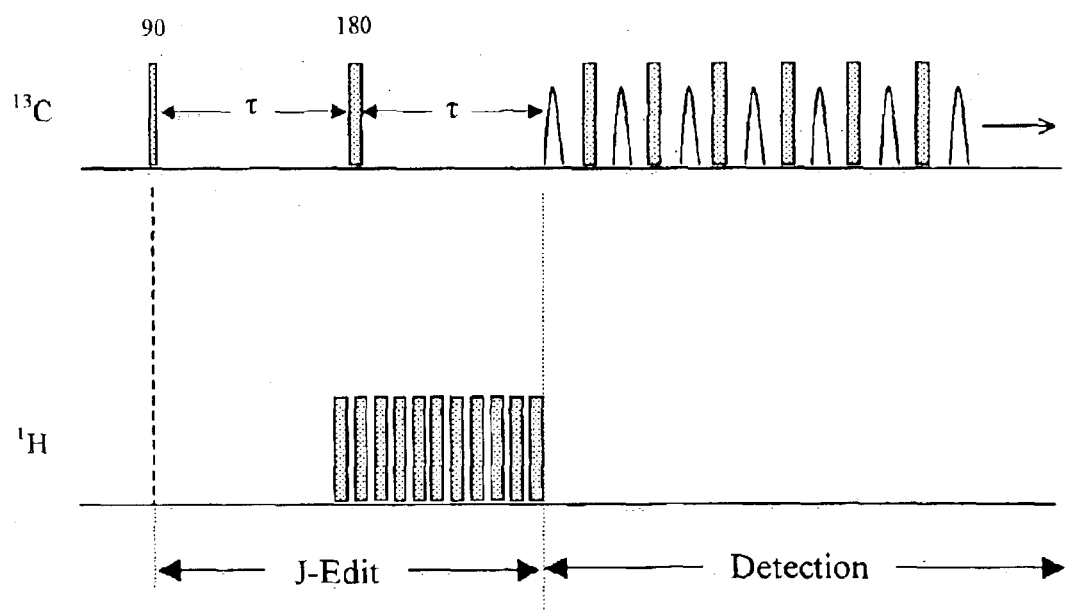
FIG. 6 shows a schematic diagram showing a pulse sequence for J editing including gated decoupling according to one embodiment of the invention.

FIG. 6 shows another embodiment of a gated-decoupling method. As shown in FIG. 6, the proton decoupler covers either the first half or the second half of the first echo spacing. In addition, the first echo spacing is varied to produce different J modulations, which are encoded in the different amplitudes of the recorded signals. This approach is similar to that shown in FIG. 4. A series of spectra may be recorded and the modulation of signal amplitudes as a function of the first echo spacing (or τ) may be analyzed (e.g., with a set of linear equations or with Fourier transformation) to provide the J coupling constants and $A_i$.

J-editing with Proton Detection

The above described embodiments are based on carbon detection and proton flipping or decoupling, i.e., $^{13}$C{$^1$H}. As noted above, carbon detection is much less sensitive compared with proton detection, due to the lower gyromagnetic ratio (γ) and the lower abundance of the carbon spin. Therefore, it is sometimes desirable to perform these experiments with proton detection, i.e., $^1$H{$^{13}$C}.

Figure 7:
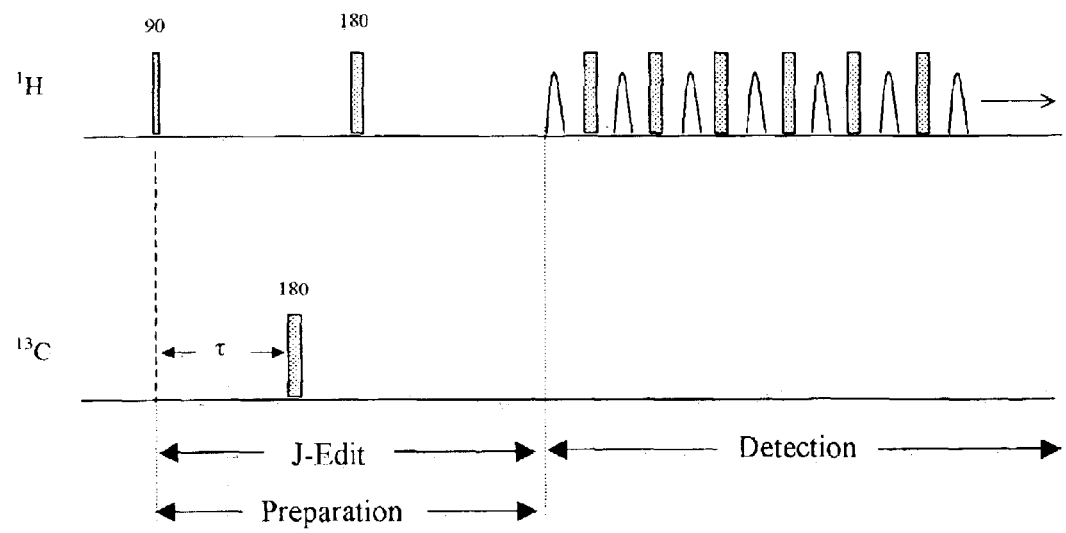
FIG. 7 shows a schematic diagram showing a pulse sequence for J editing with proton detection according to one embodiment of the invention.

FIG. 7 shows a proton detection pulse sequence similar to that shown in FIG. 2, except that the $^{13}$C and $^1$H channels are swapped. In this proton detection pulse sequence, proton spins are the source of magnetization and the subject of detection (i.e., the observed spins). Carbon spins are flipped to enable the buildup of the J-modulation. Because about 99% of the proton signal comes from protons attached to $^{12}$C and has no J coupling, the signal contribution from protons attached to $^{12}$C should be removed to facilitate analysis. This may be accomplished by subtracting the signals of two measurements, one with the carbon π pulse (i.e., J modulation) and the other without. Neglecting the field inhomogeneity effects, the first echo amplitude S(τ) after the subtraction is given by:

$$S(\tau) = \frac{0.011 \cdot S_0^h}{\sum_i A_i n_i} \sum_i A_i n_i (1 - \cos 2\pi J_i \tau) \qquad \text{Eq. (3)}$$

where the factor 0.011 is the natural abundance of $^{13}$C, $S_0^h$ is a proton spin-echo amplitude without J modulation. The terms $A_i$, $J_i$, and $n_i$ are as defined in Eq. (1).

In carbon detection methods as illustrated in FIGS. 2 and 4–6, $n_i$ changes J-modulation frequency because each carbon is simultaneously influenced by $n_i$ protons directly attached to it. In contrast, with a proton detection method as illustrated in FIG. 7, $n_i$ does not change J-modulation frequency because each proton is only influenced by one carbon directly attached to it. As a result, the proton-detection J-editing method cannot distinguish different carbon groups based on their differences in $n_i$. However, this method can still differentiate different carbon groups if they have different J-coupling constants, e.g., aromatic C—H coupling≈160 Hz, and aliphatic C—H coupling≈125 Hz. Thus, it is feasible to use this proton-detection J-editing method to distinguish aliphatics and aromatics based on different J's.

From Eq. (3), it is apparent that the signal contribution from a certain carbon group reaches its maximum value when $$\tau = \frac{1}{2} J_i \qquad \text{Eq. (4)}$$

It is also known that the J-coupling constants do not vary much among different carbon groups in oil samples, which contain mostly aliphatic hydrocarbons. Therefore, a properly selected (average) $\tau$ can be used to ensure that signal contributions from all carbon groups reach levels close to their maximum values.

One advantage of this approach is that the measured signal amplitude $S(\tau)$ is a good indication of the hydrogen index of hydrocarbons even in the presence of water in the sample. Thus, the measured signal amplitude $S(\tau)$ using the pulse sequence shown in FIG. 7 together with a regular proton measurement can be used to provide a convenient method for computing the oil/water ratio in the sample. Accordingly, this approach provides a good fluid typing method.

FIG. 7 illustrates only one exemplary pulse sequence for proton detection based on the pulse sequence shown in FIG. 2. One of ordinary skill in the art would appreciate that different proton detection J-editing pulse sequences may also be devised that are analogous to pulse sequences illustrated in FIGS. 4–6. Specifically, a pulse sequence for the proton-detection method with varied echo spacing can be obtained by swapping the $^1H$ and $^{13}C$ channels as illustrated in FIG. 4. Similarly, gated-decoupling proton-detection J-editing pulse sequences may be obtained by swapping the $^1H$ and $^{13}C$ channels illustrated in FIG. 5 and FIG. 6.

Signal Enhancement Techniques
Nuclear Overhauser Enhancement

As noted above, with carbon detection the sensitivity is low. In some methods according to the invention, the carbon detection pulse sequences may be combined with signal enhancement pulses. Various techniques are known in the art for enhancing signal amplitudes from insensitive nuclei. These techniques, for example, include Nuclear Overhauser Effects (NOE) and polarization (magnetization) transfer.

With NOE enhancement techniques, the signal amplitudes for the carbon detection J-editing methods may be enhanced by applying a proton broadband decoupler before carbon experiments. Such NOE enhancement can produce up to three times signal enhancement because the gyromagnetic ratio of a proton is about four times that of a carbon. The broad-band decoupling may be accomplished with an RF transmitter with noise modulation. Alternatively, this may be accomplished with a series of pulses with very short spacings. The duration and phase of each pulse in the series may be varied to generate broadband decoupling.

Figure 8:
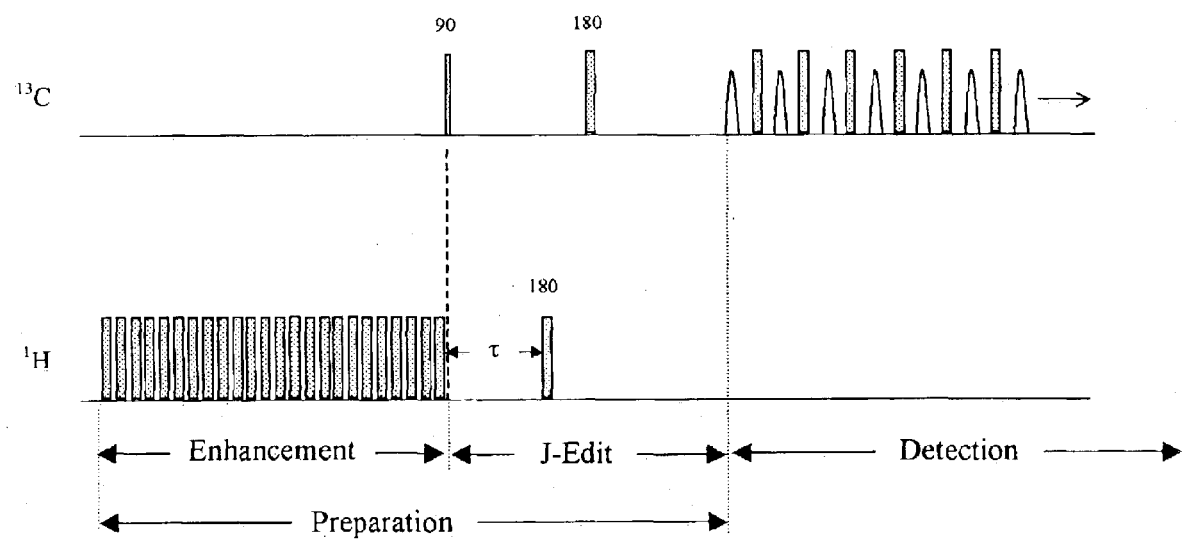
FIG. 8 shows a schematic diagram showing a pulse sequence for J editing with a signal enhancement pulse sequence according to one embodiment of the invention.
Figure 9:
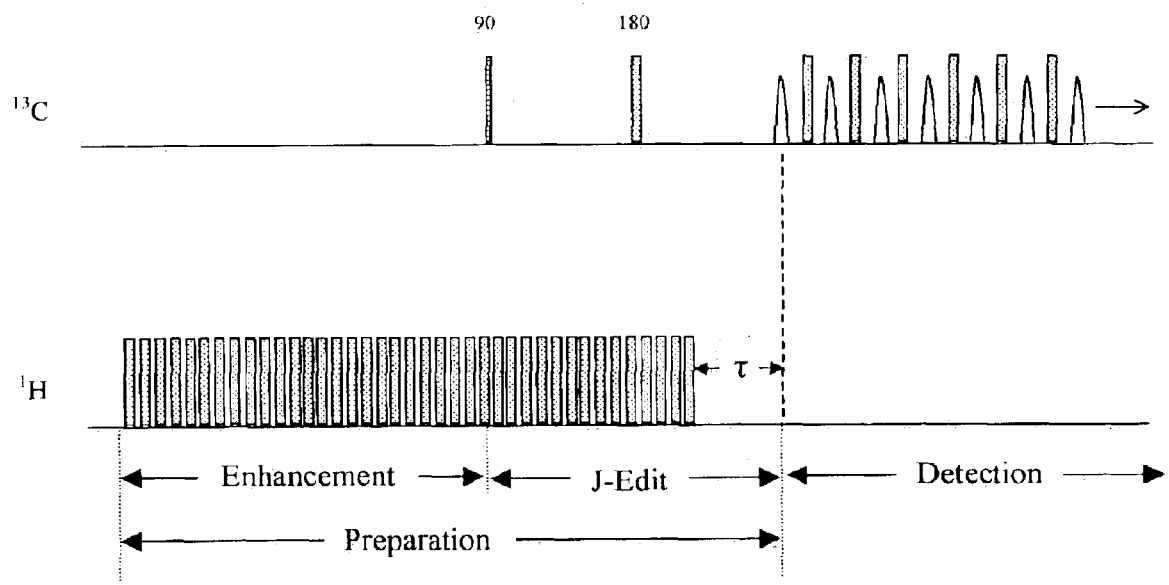
FIG. 9 shows a schematic diagram showing a pulse sequence for J editing with a signal enhancement pulse sequence and gated decoupling according to one embodiment of the invention.

FIG. 8 shows the pulse sequence of FIG. 2 combined with a NOE pulse sequence, while FIG. 9 shows a gated-decoupling J-editing pulse sequence (as shown in FIG. 5 or FIG. 6) incorporated with an NOE pulse sequence. These pulse sequences are only for illustration. One of ordinary skill in the art would appreciate that NOE decoupler/pulse sequences may be applied to all carbon detection J-editing methods. As shown in FIGS. 8 and 9, the signal enhancement pulse sequence (the NOE pulses) together with the J-Edit pulse sequence are referred to as a preparation pulse sequence. A preparation pulse sequence as used herein refers to pulse sequences prior to the detection sequence. Thus, in some embodiments, the preparation pulse sequence may include only the J-Edit pulse sequence, as shown in FIG. 7, while in other embodiments, the preparation pulse sequence may include both the signal enhancement pulse sequence and the J-edit pulse sequence, as shown in FIGS. 8 and 9.

Another approach to signal enhancement uses polarization transfer (or magnetization transfer). For example, hetero-nuclear magnetization transfer pulse sequences may be incorporated into the carbon detection J-editing methods to improve SNR. The direction of the magnetization transfer can be $^1H \rightarrow ^{13}C$, $^{13}C \rightarrow ^1H$, and $^1H \rightarrow ^{13}C \rightarrow ^1H$. The SNR of the detected signal for NMR experiments is given by $$SNR \propto \gamma_{source}(\gamma_{observe})^{3/2} \qquad \text{Eq. (5)}$$

where $\gamma_{source}$ is the gyromagnetic ratio of the source spins, $\gamma_{observe}$ the gyromagnetic ratio of the spins being detected. The proton gyromagnetic ratio $\gamma_h$ is about 4 times that of the carbon-13. Proton and carbon have different $T_1$ and $T_2$, which will also affect the SNR of the experiment. The maximum achievable SNR for the basic and signal enhanced J-editing methods are listed in Table 2. The J-editing methods with magnetization transfers use more pulses in the J-modulation buildup phase than the basic carbon detection methods. In inhomogeneous field, more pulses may result in larger errors and loss of signal due to imperfect pulses. The values listed in Table 2 represent the maximum achievable sensitivities under ideal conditions.

TABLE 2

Relative sensitivities of J-editing methods with/without magnetization transfers

| J-editing methods | Relative sensitivity (SNR) |
| --- | --- |
| Carbon detection J-editing | $(\gamma_c)^{5/2} = 1$ |
| Proton detection J-editing | $(\gamma_h)^{5/2} = 32$ |
| J-editing with $^1H \rightarrow ^{13}C$ magnetization transfer | $\gamma_h(\gamma_c)^{3/2} = 4$ |
| J-editing with $^{13}C \rightarrow ^1H$ magnetization transfer | $\gamma_c(\gamma_h)^{3/2} = 8$ |
| J-editing with $^1H \rightarrow ^{13}C \rightarrow ^1H$ magnetization transfer | $(\gamma_h)^{5/2} = 32$ |

Two common techniques for magnetization transfer include insensitive nuclei enhanced by polarization transfer (INEPT) and Hartman-Hahn Cross Polarization. The INEPT technique transfers anti-phase proton spin magnetization to anti-phase carbon spin magnetization, or vice versa. See Morris, G. A. and Freeman, R., *J. Am. Chem. Soc.*, 101, 760 (1979). This transfer is accomplished by applying a proton $\pi/2$ pulse and a carbon $\pi/2$ pulse. Using spin product operators, the magnetization transfer can be represented as:

$$2I_xS_z - (\pi/2)I_y \rightarrow -2I_zS_z - (\pi/2)S_x \rightarrow 2I_zS_y.$$

Another common technique utilizes Hartmann-Hahn cross polarization (CP). See Hartmann, S. R. and Hahn, E. L., *Phys. Rev.* 128, 2042 (1962). The proton and carbon spins are spin locked by the RF fields that satisfy the matching condition for equal precession rates in their respective rotating frames $$\gamma^h B_1^h = \gamma^c B_1^c \qquad \text{Eq. (6)}$$

where $\gamma^h$ and $\gamma^c$ are the respective gyromagnetic ratios for proton and carbon; $B_1^h$ and $B_1^c$ are the respective RF field strength for proton and carbon. Magnetization transfer occurs at half of the J-coupling frequency. This can be used to transfer magnetization from proton to carbon, or from carbon to proton.

To use the enhancement techniques in J-editing, it is necessary to design a pulse sequence having three parts: polarization, J-modulation, and detection. As noted above, the pulse sequences used in the polarization and J modulation periods may be referred to as a preparation pulse sequence. Embodiments of the invention may use various enhancement techniques (e.g., NOE, INEPT, CP) in the polarization and/or detection parts. The enhancement techniques involving NOE pulses have been described with reference to FIG. 8 and FIG. 9.

The following will describe a few exemplary pulse sequences that combine carbon-detected J-editing methods with the magnetization transfer techniques.

Figure 10:
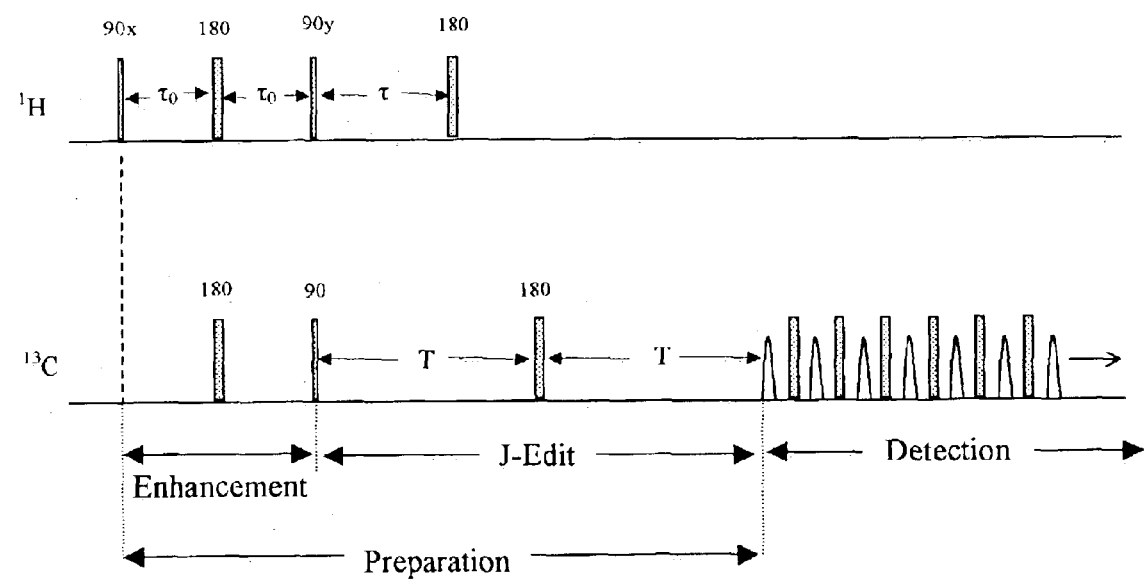
FIG. 10 shows a schematic diagram showing a pulse sequence for J editing with magnetization transfer from proton to carbon according to one embodiment of the invention.

FIG. 10 shows one embodiment of the invention using a pulse sequence for J-editing with $^1H \rightarrow ^{13}C$ magnetization transfer. As shown, the pulse sequence has three sections. In the first section ($^1H$: $(\pi/2)_x-\tau_0-(\pi)-\tau_0-(\pi/2)_y$, $^{13}C$: $(\pi)-\tau_0-(\pi/2)$), the proton magnetization is transformed into anti-phase proton magnetization through the J-coupling effect, and then is transferred into anti-phase carbon magnetization by the proton $(\pi/2)_y$ pulse and the carbon $\pi/2$ pulse. The time duration $\tau_0$ is preferably equal to $\frac{1}{4}J$ to maximize the magnetization transfer, where J is the average J-coupling constant of the sample. In the second section ($^1H$: $\tau-(\pi)$, $^{13}C$: $T-(\pi)-T$), the anti-phase carbon magnetization is refocused into carbon magnetization through the J-coupling effect. By shifting $\tau$, different amount of J-coupling effect on the carbon magnetization is achieved. The third section is the CPMG-like pulses. The carbon magnetization is detected in the form of a CPMG echo train. Multiple scans with different $\tau$ values may be acquired for computing the relative carbon group abundances, as described above.

Figure 11:
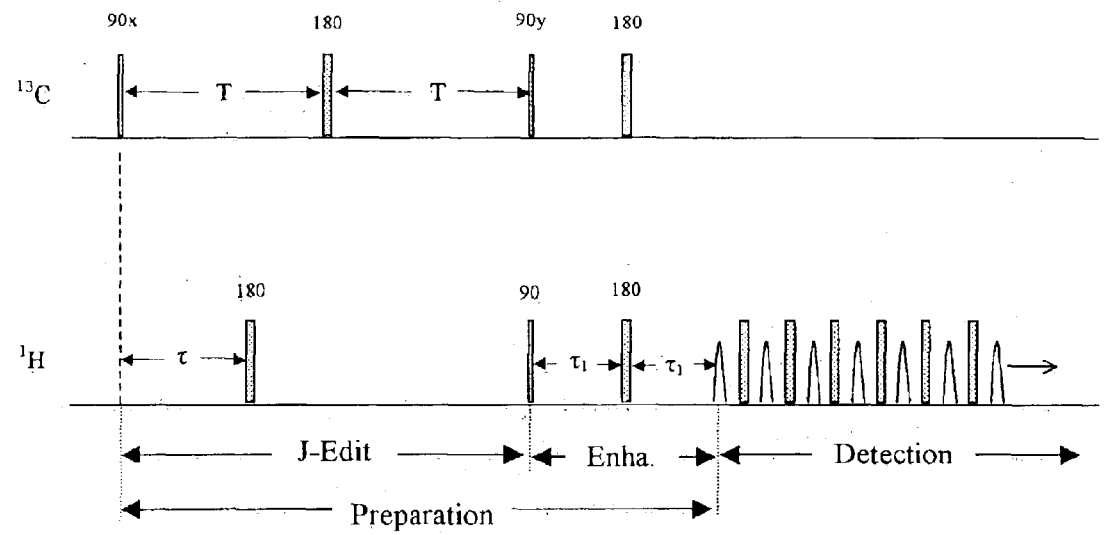
FIG. 11 shows a schematic diagram showing a pulse sequence for J editing with magnetization transfer from carbon to proton according to one embodiment of the invention.

FIG. 11 shows another embodiment of the invention involving a pulse sequence for J-editing with $^{13}C \rightarrow ^1H$ magnetization transfer. This pulse sequence also has three sections. In the first section ($^{13}C$: $(\pi/2)_x-T-(\pi)-T$, $^1H$: $\tau-(\pi)$), the carbon magnetization is transformed into anti-phase carbon magnetization through J-coupling. The amount of anti-phase carbon magnetization is changed when $\tau$ is varied. In the second section ($^{13}C$: $(\pi/2)_y-\tau_1-(\pi)$, $^1H$: $(\pi/2)-\tau_1-(\pi)-\tau_1$), the anti-phase carbon magnetization is transferred into anti-phase proton magnetization and then refocused into proton magnetization. The time duration $\tau_1$ is preferably a compromised value because carbon groups with different number of protons will behave differently. The third section of the pulse sequence is the, CPMG-like pulses, during which proton spin echo signal is detected. The proton spin echo signal has different J-modulation effect when $\tau$ is varied.

Figure 12:
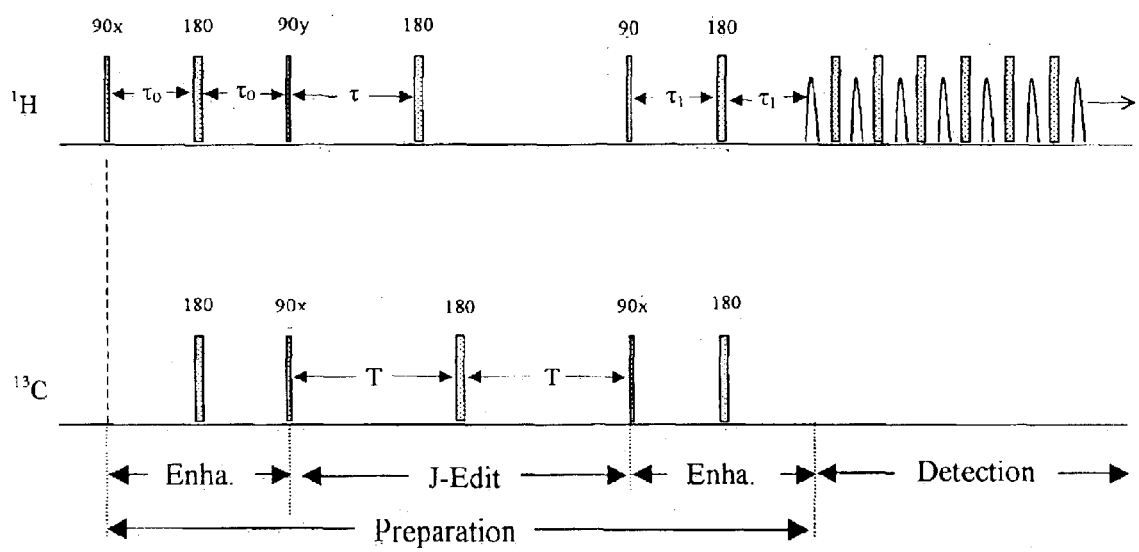
FIG. 12 shows a schematic diagram showing a pulse sequence for J editing with magnetization transfer from proton to carbon and then back to proton according to one embodiment of the invention.

FIG. 12 shows a pulse sequence for J-editing with $^1H \rightarrow ^{13}C \rightarrow ^1H$ magnetization transfer. This pulse sequence has four sections. In the first section ($^1H$: $(\pi/2)_x-\tau_0-(\pi)-\tau_0-(\pi/2)_y$, $^{13}C$: $(\pi)-\tau_0-(\pi/2)_x$), the proton magnetization is transferred into anti-phase carbon magnetization. In the second section ($^1H$: $\tau-(\pi)$, $^{13}C$: $T-(\pi)-T$), the anti-phase carbon magnetization is modulated by a factor dependent on $\tau$. In the third section ($^1H$: $(\pi/2)-\tau_1-(\pi)-\tau_1$, $^{13}C$: $(\pi/2)_x-\tau_1-(\pi)$), the anti-phase carbon magnetization is transferred into proton magnetization. In the fourth section, the proton magnetization is detected in the form of a CPMG echo train.

In all examples of magnetization transfer described above, the $\pi$ pulse after the time delay $\tau$ may be replaced by a gated decoupling pulse as previously described in the gated-decoupling J-editing methods. The gated decoupling also destroys unwanted spin coherences. Therefore, similar pulse sequences using gated decoupling are expressly within the scope of the invention.

Effects of Inhomogeneous Static and RF Fields

In deriving Eqs. (1–3) above, the field inhomogeneity effects were neglected. However, when the pulses are inaccurate or the static field inhomogeneity is comparable to RF field strength, those equations are no longer correct, which is often the case in reality, especially in downhole environments. When the inhomogeneous field effects are taken into consideration, Eq. (1) becomes $$S(\tau) = \frac{S_0^c}{jV_0} \sum_i A_i \int L_{0,-}^c \cdot \Lambda_{-,+}^c \left[ \frac{1}{2}(1 + \Lambda_{0,0}^h) + \frac{1}{2}(1 - \Lambda_{0,0}^h)\cos 2\pi J_i \tau \right]^{n_i} dv \quad \text{Eq. (7)}$$

where j is the unitary imaginary number, $V_0$ is the total volume of the sample. The symbols $L_{0,-}^c$, $\Lambda_{-,+}^c$, and $\Lambda_{0,0}^h$ are matrix elements for rotation operations due to RF pulses. In spherical notation, the magnetization vector is defined as $$M_+ = M_x + iM_y$$
$$M_- = M_x - iM_y$$
$$M_0 = M_z \quad \text{Eq. (8)}$$

The rotation of the magnetization vector due to a RF pulse is represented by a matrix R, $$\begin{pmatrix} M_+(t_p) \\ M_-(t_p) \\ M_0(t_p) \end{pmatrix} = \begin{pmatrix} R_{+,+} & R_{-,+} & R_{0,+} \\ R_{+,-} & R_{-,-} & R_{0,-} \\ R_{+,0} & R_{-,0} & R_{0,0} \end{pmatrix} \begin{pmatrix} M_+(0) \\ M_-(0) \\ M_0(0) \end{pmatrix} \quad \text{Eq. (9)}$$

where $t_p$ is the duration of the pulse. Matrix R is denoted by L for a $\pi/2$ pulse and $\Lambda$ for a $\pi$ pulse. Furthermore, $L^c$ and $\Lambda^c$ denote matrices for carbon $\pi/2$ and $\pi$ pulses, respectively, $L^h$ and $\Lambda^h$ denote matrices for proton $\pi/2$ and $\pi$ pulses, respectively. The matrix elements $L_{0,-}^c$, $\Lambda_{-,+}^c$, and $\Lambda_{0,0}^h$ in Eq. (7) are given by $$L_{0,-}^c = \frac{\omega_1^c}{\Omega^c} \left\{ \frac{\Delta \omega_0^c}{\Omega^c} [1 - \cos(\Omega^c t_{\pi/2}^c)] + j\sin(\Omega^c t_{\pi/2}^c) \right\} \exp(j\phi_{\pi/2}^c) \quad \text{Eq. (10)}$$

$$\Lambda_{-,+}^c = \frac{1}{2}\left(\frac{\omega_1^c}{\Omega^c}\right)^2 [1 - \cos(\Omega^c t_\pi^c)]\exp(-j2\phi_\pi^c) \quad \text{Eq. (11)}$$

$$\Lambda_{0,0}^h = \left(\frac{\Delta\omega_0^h}{\Omega^h}\right)^2 + \left(\frac{\omega_1^h}{\Omega^h}\right)^2 \cos(\Omega^h t_\pi^h). \quad \text{Eq. (12)}$$

The carbon Larmor frequency offset $\Delta\omega_0^c$ is defined as $\Delta\omega_0^c = \gamma^c B_0 - \omega_{RF}^c$, where $\gamma^c$ is the gyromagnetic ratio of $^{13}C$, $B_0$ the static magnetic field strength, and $\omega_{RF}^c$ the RF angular frequency for carbon. The term $\omega_1^c$ is defined as $\omega_1^c = \gamma^c B_1^c/2$ where $B_1^c$ is the RF field strength for carbon. The carbon nutation frequency is given by $\Omega^c = \sqrt{(\Delta\omega_0^c)^2 + (\omega_1^c)^2}$. The time durations of the carbon $\pi/2$ and $\pi$ pulses are denoted by $t_{\pi/2}^c$ and $t_\pi^c$, respectively, and the phases of those pulses are denoted by $\phi_{\pi/2}^c$ and $\phi_\pi^c$, respectively. The proton related terms $\Delta\omega_0^h$, $\omega_1^h$, $\Omega^h$, $t_\pi^h$ are defined similarly as those corresponding terms for carbon. The integral in Eq. (7) integrates over the whole volume of the sample.

The matrix elements to $L_{0,-}^c$, $\Lambda_{-,+}^c$, and $\Lambda_{0,0}^h$ can be theoretically computed after the static and RF fields are carefully mapped. Alternatively, these parameters can be found through calibration using some oil samples whose compositions are already known. In general, five parameters need to be found through calibration, which are $\int L_{0,-}^c \Lambda_{-,+}^c dv$, $\int L_{0,-}^c \Lambda_{-,+}^c \Lambda_{0,0}^h dv$, $\int L_{0,-}^c \Lambda_{-,+}^c (\Lambda_{0,0}^h)^2 dv$, $\int L_{0,-}^c \Lambda_{-,+}^c (\Lambda_{0,0}^h)^3 dv$, and $\int L_{0,-}^c \Lambda_{-,+}^c (\Lambda_{0,0}^h)^4 dv$. After these five parameters are determined, $S(\tau)$ becomes $4^{th}$ order polynomial of $\cos 2\pi\tau J_i$. The abundance of different carbon groups can then be resolved by the means previously described for solving Eq. (1).

Eq. (7) looks complicated. However, all complications come from the term $\Lambda_{0,0}{}^h$. If the proton π pulse is perfect everywhere in the sample, $\Lambda_{0,0}{}^h$ becomes −1. The term $$\left[\frac{1}{2}(1+\Lambda_{0,0}^h)+\frac{1}{2}(1-\Lambda_{0,0}^h)\cos 2\pi J_i\tau\right]^{n_i}$$

in Eq. (7) may then be simplified to $[\cos 2\pi J_i\tau]^{n_i}$, which can then be taken out of the integral because it is not spatially dependent. With that simplification, Eq. (7) becomes Eq. (1) except for a constant factor $\int L_{0,-}{}^c \Lambda_{-,+}{}^c dv$ that can be derived from calibration.

Although it is difficult to have perfect proton π pulse everywhere in the sample in inhomogeneous fields, it is possible to avoid/minimize the J-modulation buildup after the imperfect proton π pulse, for example, using a gated-decoupling carbon-detection pulse sequence. The decoupling pulses should completely decouple the proton-carbon J-coupling such that Eq. (2) is correct even in inhomogeneous fields. Complete decoupling is achievable by using proper decoupling pulses or an RF transmitter coupled with a noise modulator to produce a broad band decoupling pulse.

For carbon-flip proton-detection J-editing, Eq. (3) changes to the following form when the field inhomogeneity effects are taken into account:

$$S(\tau) = \frac{1}{2}\int L_{0,-}^h \Lambda_{-,+}^h (1-\Lambda_{0,0}^c) dv \frac{0.011 \cdot S_0^h}{\sum_i A_i n_i} \sum_i A_i n_i (1-\cos 2\pi J_i \tau). \qquad \text{Eq. (13)}$$

The term $$\frac{1}{2}\int L_{0,-}^h \Lambda_{-,+}^h (1-\Lambda_{0,0}^c) dv$$

is a constant factor, which may be easily calibrated. The matrix elements $L_{0,-}{}^h$, $\Lambda_{-,+}{}^h$, and $\Lambda_{0,0}{}^c$ are analogous to $L_{0,-}{}^c$, $\Lambda_{-,+}{}^c$, and $\Lambda_{0,0}{}^h$ that are given in Eqs. (10–12).

Figure 13:
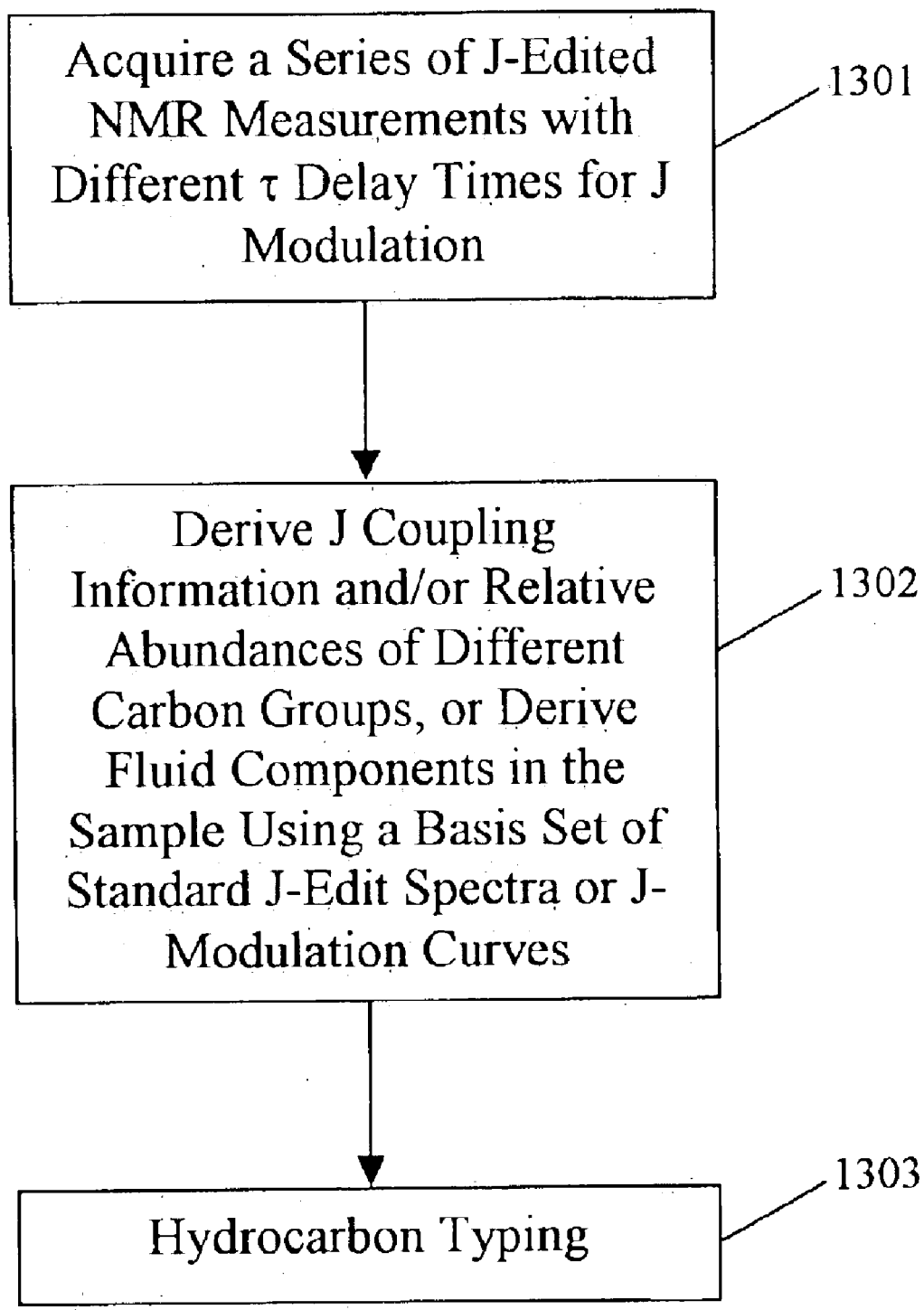
FIG. 13 shows a flow chart of a method for deriving J coupling and for hydrocarbon typing according to one embodiment of the invention.

FIG. 13 illustrate a method in accordance with one embodiment of the invention for obtaining J coupling information using J editing. As shown in step 1301, a series of J-edited NMR measurements are acquired with different τ delay times to the development of J modulations. These measurements may be performed with any of the pulse sequences illustrated in the present invention or with modified sequences that are analogous to those shown. A typical pulse sequence for this purpose may include two parts: the first part is a "preparation pulse sequence," which may include only a J-edit pulse sequence or additionally include a signal enhancement pulse sequence, and the second part is a "detection sequence." The J-edit pulse sequence permits J coupling to develop during a selected delay time τ to modulate the detected signal amplitudes. The J-edit pulse sequence may include a pulse or a composite pulse to flip the coupled nuclear spins or a decoupling pulse to decouple the coupled nuclear spins. As noted above, the J-edit sequence may be used to develop J modulation for the first echo or for the first few echoes. The "detection sequence" may simply be a wait time (i.e., includes no pulse sequence) for the detector to acquire the first echo signal that resulted from the preparation pulse sequence. Alternatively, the detection sequence may include one or more π pulses to induce further echoes. When the detection sequence includes a plurality of π pulses, the overall sequence, including the preparation pulse sequence, is reminiscent of a CPMG pulse sequence. Such a CPMG-like sequence (i.e., a plurality of π pulses) may be used to collect a large number of spin echoes in a relative short period of time to improve the SNR.

As shown in step 1302, the series of NMR measurements are then used to derive the J coupling information and/or the relative abundances of the carbon groups. This derivation may be performed by solving a series of linear equations that define the signal amplitudes as a function of the delay time τ. Alternatively, this may be performed with a Fourier transformation, if the different τ values are incremented by the same amount. The derivation involves correlating the signal amplitudes with the delay time τ using a selected function that is based on the pulse sequence used in the data acquisition, e.g., Eq. (1)–(3), (7), and (13).

The above described methods derive the J-coupling information to obtain the relative abundances of the carbon groups. In an alternative approach, the J-edit spectrum (or the J-modulation curve as a function of delay time τ) of a formation fluid may be deconvoluted into weighted contributions from a basis set of J-edit spectra (or J-modulation curve) recorded with standard samples having known compositions (e.g., methane, heavy oil, medium oil, light oil, and oil-based mud). The deconvolution may be accomplished by performing eigenanalysis based on the basis set of J-edit spectra or J-modulation curves. The relative weights of the basis set represent the relative abundances of the standard fluid types in the formation fluid. This alternative approach does not involve derivation of the J-coupling information. Instead, it directly provides relative abundances of various fluids in the formation fluid sample. This approach is not sensitive to magnetic field inhomogeneity and, therefore, no correction for the filed inhomogeneity is necessary.

In some embodiments, the method may further include a step for hydrocarbon typing based on the derived J coupling constants and the relative abundances of the carbon groups ($A_i$) (shown as step 1303). For example, if the J coupling constants include a population of 160 Hz, then the sample includes aromatics. Similarly, J coupling of 125 Hz indicates the presence of aliphatic hydrocarbons. The relative contents of various hydrocarbons may be further classified based on the relative abundance $A_i$ and $n_i$.

Figure 14:
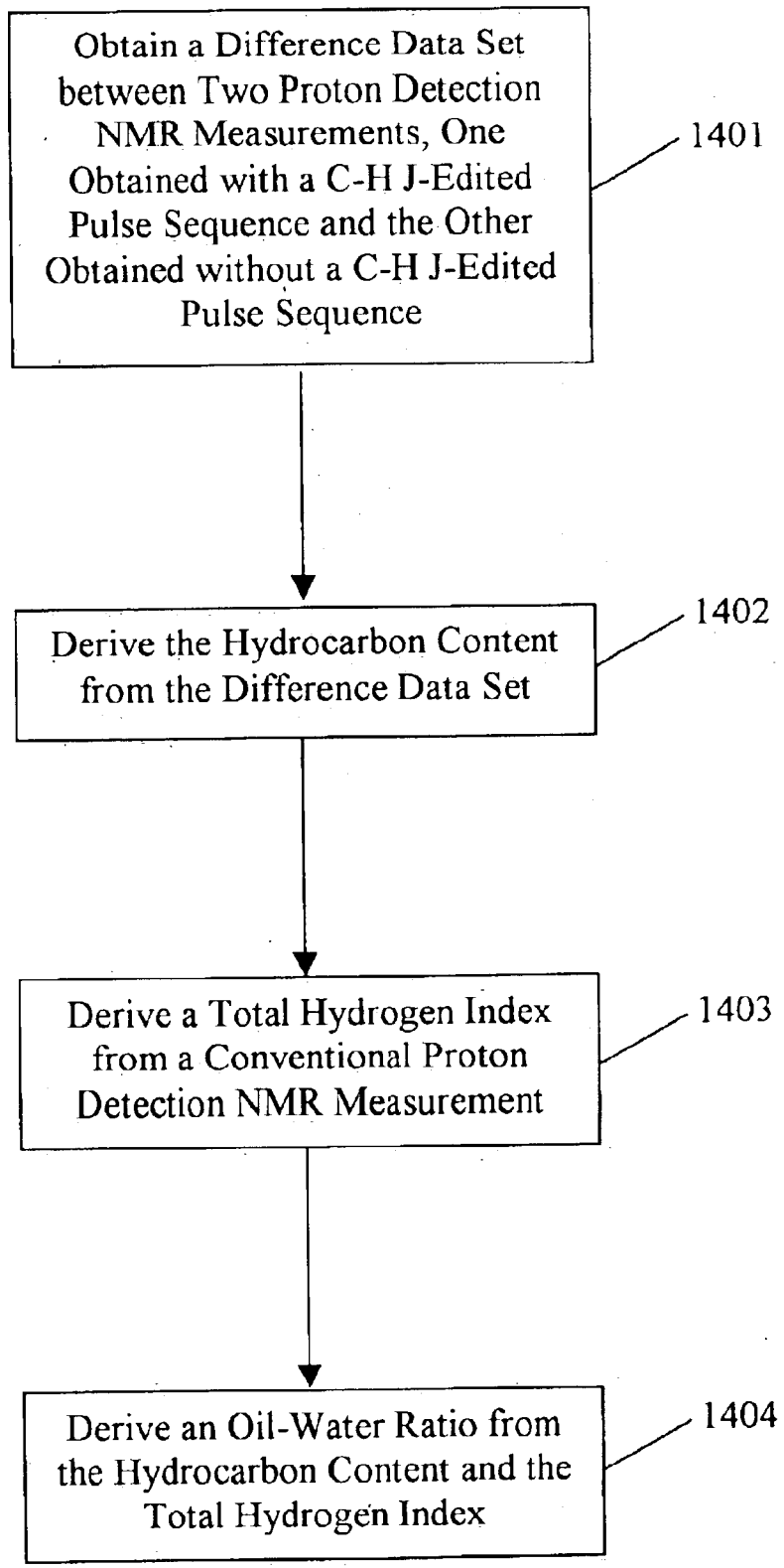
FIG. 14 shows a flow chart of a method for calculating oil-water ratios and for fluid typing according to one embodiment of the invention.

FIG. 14 shows a method in accordance with the invention for fluid typing. As shown in step 1401, a difference data set is obtained with proton detection. The difference is between two measurements, one with J modulation and the other without. The difference data set would include only those protons having $^{13}C$ nuclei attached to them. Proton signals due to protons not attached to $^{13}C$ nuclei are removed, including those signals from water.

In step 1402 a hydrocarbon content (index) is derived from the difference data set. In deriving the hydrocarbon index, it is necessary to take into account that only about 1.1% of carbons in nature are carbon-13 species.

In step 1403 the total hydrogen index is obtained with a conventional NMR measurement, which measures all signals from hydrogen species, be it from water or hydrocarbons. This total hydrogen index together with the hydrocarbon index can then be used to derive the relative abundance of water and hydrocarbons in the fluid sample. From the relative abundances of water and hydrocarbons, it is then possible to calculate the oil-water ratio or for fluid typing (shown as step 1404).

Advantageously, the embodiments of the present invention provide convenient methods for determining relative abundance and types of various carbon groups, including quaternary C, aromatic CH, aliphatic CH, $CH_2$, $CH_3$, and CH$_4$. Methods in accordance with the invention are based on J coupling and are less sensitive to magnetic field inhomogeneity compared to prior art methods. Because these methods are less sensitive to magnetic field inhomogeneity, embodiments of the invention may be used in a laboratory or in an environment where magnetic field homogeneity is difficult to obtain, for example, in a wellbore.

The carbon group information obtained with methods of the invention may be used in many applications: measurement of hydrogen index of hydrocarbons in the presence of water, methane gas detection from the CH$_4$ abundance; CH$_2$/CH$_3$ ratio estimation, which is a good indicator of average chain length of the molecules; aromatics/aliphatics ratio determination, the abundance of aliphatic CH, which is related to branching and affects wax formation; and quaternary C estimation as an indication of asphaltene, to name a few. In addition, carbon group abundances thus determined may provide useful inputs for molecular weight analysis based on diffusion or T$_2$ distributions.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for determining with a downhole tool an oil-to-water ratio in a fluid sample, comprising:
    obtaining a nuclear magnetic resonance data set representing protons attached to carbon-13 in the fluid sample;
    deriving a hydrocarbon content from the nuclear magnetic resonance data set, taking into account a natural abundance of carbon-13;
    acquiring a total nuclear magnetic resonance for all protons in the fluid sample, wherein the fluid sample is subject to a primarily inhomogeneous static magnetic field;
    deriving a total hydrogen index from the total nuclear magnetic resonance measurement; and
    deriving the oil-to-water ratio of the fluid sample from the hydrocarbon content and the total hydrogen index.

2. The method of claim 1, wherein the nuclear magnetic resonance data set is obtained by subtracting a first proton nuclear magnetic resonance measurement acquired with a J-edit pulse sequence from a second proton nuclear magnetic resonance measurement acquired without a J-edit pulse sequence.

3. A nuclear magneticresonance instrument, comprising:
    a housing adapted to move in a wellbore;
    a magnet disposed in the housing adapted to induce a static magnetic field in a zone of interest, the static magnetic field being primarily inhomogeneous in the zone of interest;
    an antenna assembly disposed in the housing, the antenna assembly adapted to induce an oscillating magnetic field in the zone of interest and to receive nuclear magnetic resonance signals; and
    an electronic module including a memory to store instructions for performing a J-edit pulse sequence.

4. The instrument of claim 3, wherein the housing is adapted to be lowered into the wellbore on an electric cable.

5. The instrument of claim 3, wherein the housing forms part of a drilling tool assembly.

6. The instrument of claim 3, wherein the housing forms part of a formation fluid sampling tool.

7. A method for obtaining nuclear magnetic resonance measurements in a wellbore, comprising:
    inducing a static magnetic field in a fluid sample, the static magnetic field being primarily inhomogeneous in the fluid sample;
    applying an oscillating magnetic field to the fluid sample according to a preparation pulse sequence that comprises a J-edit pulse sequence for developing J modulation; and
    acquiring the nuclear magnetic resonance measurements using a detection sequence, wherein the detection sequence comprises at least one 180-degree pulse.

8. The method of claim 7, wherein the J modulation is based on a heteronuclear coupling.

9. The method of claim 8, wherein the heteronuclear coupling is carbon-proton coupling.

10. The method of claim 9, wherein the J-edit pulse sequence includes a variable delay and the applying and the acquiring are performed a plurality of times to provide a plurality of nuclear magnetic resonance measurements each with a different value for the variable delay.

11. The method of claim 10, further comprising analyzing amplitudes of the plurality of nuclear magnetic resonance measurements as a function of the variable delay to provide J coupling information or relative abundance of carbon groups.

12. The method of claim 11, wherein the analyzing comprises solving a set of linear equations or performing a Fourier transformation.

13. The method of claim 11, further comprising determining types of hydrocarbons present in the fluid sample.

14. The method of claim 10, further comprising analyzing amplitudes of the plurality of nuclear magnetic resonance measurements to derive a composition of the fluid sample, wherein the analyzing is performed using a basis set of measurements obtained with standard samples having known compositions.

15. The method of claim 10, further comprising deriving a J-modulation curve describing amplitudes of the plurality of nuclear magnetic resonance measurements as a function of the variable delay; and comparing the J-modulation curve with a basis set of standard J-modulation curves to derive a composition of the fluid sample, wherein the basis set of the standard J-modulation curves are obtained with standard samples having known compositions.

16. The method of claim 7, wherein the fluid sample is located in an earth formation.

17. The method of claim 7, wherein the fluid sample is removed from an earth formation by a formation tester.

18. The method of claim 10, wherein the nuclear magnetic resonance measurements comprise proton signals.

19. The method of claim 10, wherein the nuclear magnetic resonance measurements comprise carbon signals.

20. The method of claim 7, wherein the preparation pulse sequence further comprises a signal enhancement pulse sequence.

21. The method of claim 20, wherein the signal enhancement pulse sequence is a nuclear Overhauser enhancement pulse sequence or a magnetization transfer pulse sequence.

22. The method of claim 7, wherein the J-edit pulse sequence includes a gated-decoupling pulse.

23. A method for characterizing formation fluids, comprising:
    disposing a nuclear magnetic resonance instrument in a borehole;
    inducing a static magnetic field in a fluid sample in a region of interest, the static magnetic field being primarily inhomogeneous in the fluid sample;

applying an oscillating magnetic field to the fluid sample according to a preparation pulse sequence that comprises a J-edit pulse sequence for developing J modulation; and acquiring nuclear magnetic resonance measurements using a detection sequence, wherein the detection sequence comprises at least one 180-degree pulse.

24. The method of claim 23, wherein the region of interest is in an earth formation.

25. The method of claim 23, wherein the region of interest is inside the nuclear magnetic resonance instrument.

26. The method of claim 23, wherein the J-edit pulse sequence includes a variable delay and the applying and the acquiring are performed a plurality of times to provide a plurality of nuclear magnetic resonance measurements each with a different value for the variable delay.

27. The method of claim 26, further comprising analyzing amplitudes of the plurality of nuclear magnetic resonance measurements as a function of the variable delay to provide J coupling information or relative abundance of carbon groups.

28. The method of claim 27, further comprising determining hydrocarbon types in the fluid sample.

29. The method of claim 26, further comprising analyzing amplitudes of the plurality of nuclear magnetic resonance measurements to derive a composition of the fluid sample, wherein the analyzing is performed using a basis set of measurements obtained with standard samples having known compositions.

30. The method of claim 26, further comprising deriving a J-modulation curve describing amplitudes of the plurality of nuclear magnetic resonance measurements as a function of the variable delay; and comparing the J-modulation curve with a basis set of standard J-modulation curves to derive a composition of the fluid sample, wherein the basis set of the standard J-modulation curves are obtained with standard samples having known compositions.

* * * * *